(12) United States Patent
Vogel

(10) Patent No.: US 12,178,508 B2
(45) Date of Patent: Dec. 31, 2024

(54) MEDICAL INSTRUMENT AND METHOD FOR PRODUCING SAME

(71) Applicant: ALLEIMA KARLSRUHE GMBH, Karlsruhe (DE)

(72) Inventor: Bernd Vogel, Karlsruhe (DE)

(73) Assignee: Alleima Karlsruhe GmbH, Karlsruhe (DE)

( * ) Notice: Subject to any disclaimer, the term of this patent is extended or adjusted under 35 U.S.C. 154(b) by 474 days.

(21) Appl. No.: 17/613,146

(22) PCT Filed: May 26, 2020

(86) PCT No.: PCT/EP2020/000103
§ 371 (c)(1),
(2) Date: Nov. 22, 2021

(87) PCT Pub. No.: WO2020/239249
PCT Pub. Date: Dec. 3, 2020

(65) Prior Publication Data
US 2022/0218416 A1  Jul. 14, 2022

(30) Foreign Application Priority Data
May 28, 2019 (EP) .................................... 19000261

(51) Int. Cl.
*A61B 18/26* (2006.01)
*H01S 3/067* (2006.01)
(Continued)

(52) U.S. Cl.
CPC .......... *A61B 18/26* (2013.01); *H01S 3/06716* (2013.01); *H01S 3/1616* (2013.01);
(Continued)

(58) Field of Classification Search
CPC .......... A61B 18/26; A61B 2017/00526; A61B 2017/00845; A61B 2017/00867;
(Continued)

(56) References Cited

U.S. PATENT DOCUMENTS 6,264,664 B1   7/2001  Avellanet
2002/0026203 A1  2/2002  Bates et al.
(Continued)

FOREIGN PATENT DOCUMENTS

DE   36 33 527    4/1988
EP   1 018 953    7/2000

OTHER PUBLICATIONS

Wilson et al.: A Miniaturized, 1.9F Integrated Optical Fiber and Stone Basket for Use in Thulium Fiber Laser Lithotripsy, Journal of Endourology, vol. 29, No. 10, Oct. 2015, pp. 1110-1114 (cited in specification, p. 2, lines 12-19).

*Primary Examiner* — Scott M. Getzow
(74) *Attorney, Agent, or Firm* — Morgan, Lewis & Bockius LLP

(57) ABSTRACT

The present invention relates to a medical instrument (1), comprising a tool (10), a catheter assembly and a handle (20), by means of which the tool (10) can be actuated, and to a method for producing the medical instrument. The tool (10) is a wire construction having at least two wire portions (11', 11", 12', 12", 13', 13") and is arranged at a distal end of the catheter assembly. The catheter assembly is formed from an outer tube (3) and an inner tube (4), which is arranged coaxially to the outer tube. Furthermore, the medical instrument (1) has an optical waveguide (2), which extends through the inner tube (4) and the exit end (2') of which opens into a space delimited by the tool (10). At least one first wire portion (11', 12', 13') is fastened, at a proximal end (11a, 12a, 13a) thereof, to the distal end of the inner tube (4), and at least one second wire portion (11", 12", 13") is
(Continued)

DETAIL D fastened, at a proximal end (11*b*, 12*b*, 13*b*) thereof, to the distal end of the outer tube (3). The outer tube (3) and the inner tube (4) are movable relative to one another, and the tool (10) can be actuated for opening and closing by means of the relative movement between the outer tube (3) and the inner tube (4). The medical instrument (1) does not have a guide wire for actuating the tool (10).

18 Claims, 6 Drawing Sheets

(51) Int. Cl.
*H01S 3/16* (2006.01)
*A61B 17/00* (2006.01)
*A61B 17/221* (2006.01)
*A61B 18/00* (2006.01)
*A61B 18/22* (2006.01)

(52) U.S. Cl.
CPC ............... *A61B 2017/00526* (2013.01); *A61B 2017/00845* (2013.01); *A61B 2017/00867* (2013.01); *A61B 2017/2212* (2013.01); *A61B 2018/00946* (2013.01); *A61B 2018/2222* (2013.01)

(58) Field of Classification Search
CPC .. A61B 2017/2212; A61B 2018/00946; A61B 2018/2222; A61B 2017/00367; A61B 17/221; H01S 3/06716; H01S 3/1616; H01S 3/06704
See application file for complete search history.

(56) References Cited

U.S. PATENT DOCUMENTS

2002/0068943 A1 6/2002 Chu et al.
2019/0117309 A1 4/2019 Shelton

DETAIL D

Fig. 8
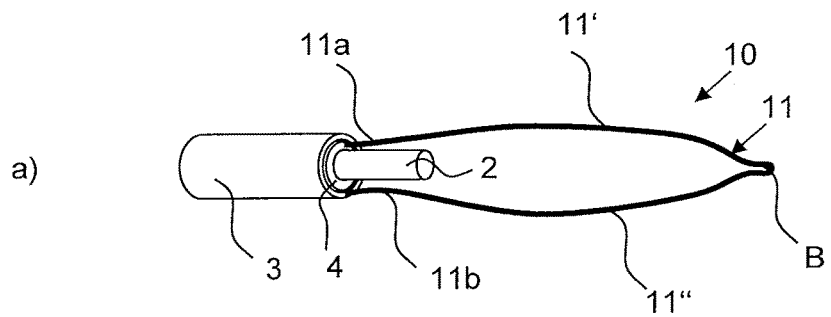
a)
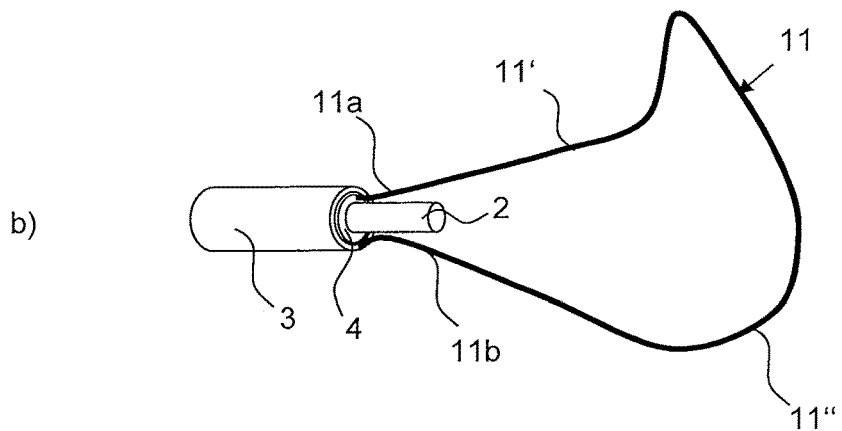
b)
Fig. 9
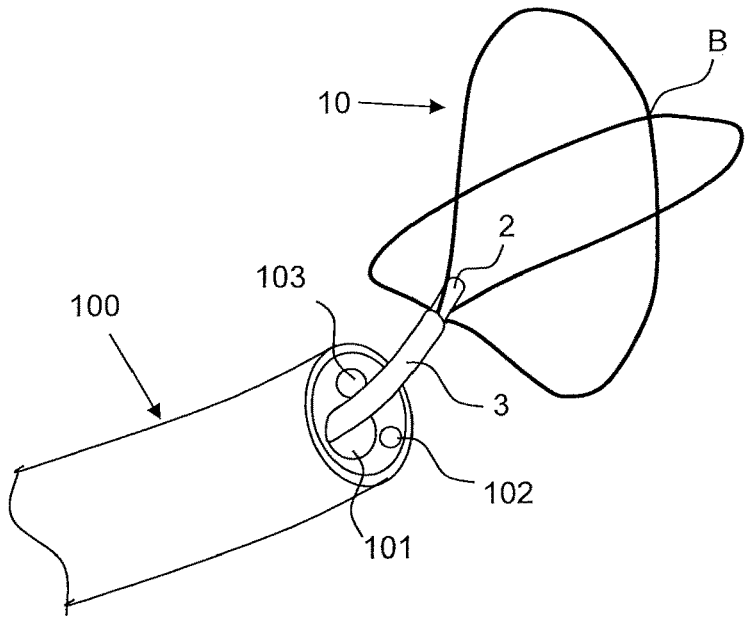

MEDICAL INSTRUMENT AND METHOD FOR PRODUCING SAME

BACKGROUND OF THE INVENTION

The invention concerns a medical instrument with a tool that is in particular a stone basket and with an optical waveguide such as a laser fiber as well as a method for producing this medical instrument.

It is known from the prior art to employ for breaking up concrements in hollow organs, for example, bile duct or kidney stones, laser lithotripters with a capturing device such as a stone basket with which a concrement is held while it is comminuted or destroyed by the lithotripter by means of laser light pulses. In this context, stone basket and laser lithotripter can be guided in the working channels of two separate endoscopic instruments whereby advantageously a satisfactory flushing of the working field is ensured, but disadvantageously the exact positioning of basket and waveguide tip relative to each other is difficult in order to be able to destroy a concrement captive in the basket without damaging by laser pulses the wire slings of the stone basket, also referred to as basket wires, or even the surrounding tissue.

US 2002/0068943 A1 discloses a capturing instrument that is not guided in combination with a laser lithotripter, wherein the wire slings are of a material that is resistant to laser induced damages and can be moved in and out within an outer sleeve by attachment to an inner pulling wire.

EP 1 018 953 A1 shows such a capturing instrument with a basket formed of several wire sections whose ends extend through an outer hollow shaft to the handpiece, are fastened at one or several inner guide elements slidably arranged within the outer shaft or directly at the shaft.

In order to ensure a targeted safe application of the laser energy on the concrement, DE 36 33 527 A1 discloses an instrument in which the stone basket can be extended coaxially to an axially displaceable optical waveguide in order to be able to fix stones with the basket and to place the waveguide centrally onto the stone in order to break it apart without touching surrounding tissue. The instrument comprises an outer tube in which the laser light guide, a pulling wire for the basket, and the basket wires attached thereto can be guided. For coaxial arrangement of the laser light guide with the stone basket, the laser light guide that is surrounded by an inner tube of inert material is guided at the distal end in a (metal) guide sleeve with a bore. This guide sleeve is arranged in the outer tube and comprises at the outer wall surface longitudinal grooves in which the basket wires are guided. Due to the given diameter of the laser fiber, diameters of the inner tube, of the guide sleeve, and of the outer tube build up to an outer diameter of up to 3.2 mm, which affects the flexibility of the instrument and also permits flushing of the working region only to a limited extent with this instrument because the guide sleeve, in whose bore the light guide with the surrounding inner tube is received, enables the supply of flushing water substantially only through the longitudinal grooves.

In this field, Wilson et al. in "A Miniaturized, 1.9 F Integrated Optical Fiber and Stone Basket for Use in Thulium Fiber Laser Lithotripsy", Journal of Endourology, vol. 29, No. 10 Oct. 2015, pages 1110-1114, discloses also the use of a thulium laser by utilizing a laser fiber with reduced outer diameter of 140 µm in a miniaturized instrument in which laser fiber and stone basket are used in combination. The laser fiber is arranged adjacent to a 1.3 F (433 µm) stone basket and its handling wire in a 1.9 F (633 µm) insertion envelope so that laser fiber and stone basket are provided together but not coaxial.

Moreover, U.S. Pat. No. 6,264,664 B1 discloses an instrument with a basket and a light guide wherein the light guide is present in an inner tube at which the proximal end of the basket is attached at the same time. The inner tube is positioned in an outer sleeve and can be moved relative thereto so that the basket with shape memory opens upon exit from the outer sleeve.

Based on this prior art, it is object of the present invention to improve a stone basket with integrated optical waveguide in such a manner that laser-induced damages at the stone basket and damages at the optical waveguide are reduced.

SUMMARY OF THE INVENTION

This object is solved by a medical instrument with a tool, a catheter assembly, and a handle, with which the tool can be actuated, which is a wire structure with at least two wire sections and which is arranged at a distal end of the catheter assembly, which is comprised of an outer tube and an inner tube arranged coaxially thereto, wherein the outer tube and the inner tube are movable relative to each other, and wherein the medical instrument moreover comprises an optical waveguide that extends through the inner tube and whose exit end ends coaxially in a space delimited by the tool, and wherein the medical instrument comprises no guide wire for actuation of the tool, characterized in that at least a first wire section with a proximal end is fastened to the distal end of the inner tube and at least a second wire section with a proximal end is fastened to the distal end of the outer tube, and in that the tool for opening and closing is actuatable by the relative movement between the outer tube and the inner tube.

The further object of producing such a medical instrument is solved by the method for producing a medical instrument according to the invention, comprising the steps:

forming a tool of at least two wire sections to a wire structure and providing a catheter assembly of an outer tube and an inner tube coaxially arranged thereto and movable relative thereto, fastening a proximal end of at least one first wire section to the distal end of the inner tube, and fastening a proximal end of at least one second wire section to the distal end of the outer tube so that the tool is actuatable for opening and closing by the relative movement between the outer tube and the inner tube without guide wire, and coaxially inserting the optical waveguide into and through the inner tube so that an exit end of the optical waveguide ends coaxially in a space delimited by the tool.

Further embodiments are disclosed in the respective dependent claims.

A first embodiment of the medical instrument according to the invention comprises a tool, a catheter assembly, and a handle with which the tool that is a wire structure with at least two wire sections can be actuated. The handle is arranged at a distal end of the catheter assembly. The catheter assembly is formed in this context of an outer tube and an inner tube that is arranged coaxially thereto. The medical instrument comprises moreover an optical waveguide which extends through the inner tube and whose exit end ends in a space which is delimited by the tool. According to the invention, in this context at least a first wire section of the wire structure is fastened with a proximal end to the distal end of the inner tube and at least a second wire section of the wire structure with the proximal end to the distal end of the outer tube. In this context, the outer tube and the inner tube are movable relative to each other so that the tool for opening and closing can be actuated by the relative movement between the outer tube and the inner tube wherein the wire ends are moved relative to each other and the wire structure can be deformed thereby. Thus, the medical instrument advantageously does not require a guide wire for actuating the tool.

The tool, according to an embodiment according to the invention, can be a grasping or capturing tool such as a stone basket.

In that the medical instrument requires no guide wire for actuating the tool, it differs advantageously from conventional instruments in which a guide wire extends from the tool (a stone basket or another grasping tool) through the tube assembly to the handle.

The catheter assembly of the outer tube movable relative to the inner tube takes over the function of the guide wire and permits, with the arrangement of the optical waveguide in the inner tube which is guided directly in the outer tube, a coaxial arrangement of the optical waveguide exit in the space which is delimited by the tool without further means or measures for protection of the optical waveguide in relation to a guide wire being required. In this way, the diameter of the catheter assembly with the coaxial optical waveguide can be advantageously significantly reduced, which improves the flexibility of the instrument. In this context, the diameter of the optical waveguide, of the inner and outer tubes are matched relative to each other so that no or hardly any clearance between the optical waveguide, inner and outer tube exists, i.e., the inner diameter of the inner tube corresponds to the diameter of the optical waveguide and the inner diameter of the outer tube corresponds to the outer diameter of the inner tube, within a tolerance range, respectively, that permits guiding and displacement within each other.

The laser fiber as well as the inner diameter of the tube have manufacturing tolerances. The clearance between these two components, as is known to a person of skill in the art, must be designed accordingly so that the laser fiber can be displaced even in the worst case, for the greatest possible diameter of the laser fiber and smallest possible inner diameter of the tube. Based on this concept, a clearance in the order of magnitude of 10% of the laser fiber diameter can be presumed.

In addition, the coaxial arrangement of the optical waveguide exit in the space delimited by the tool enables directing a light beam centrally onto an object grasped by the tool, e.g., breaking up a stone captured by a stone basket with a laser beam centrally directed thereon without touching surrounding tissue. This risk exists when stone basket and light guiding fiber are arranged adjacent to each other.

In a further embodiment of the medical instrument, the design of the optical waveguide as a laser fiber embodied for guiding laser radiation of a thulium laser, which enables utilization of a laser fiber with significantly reduced diameter of 200 µm and smaller, provides a further improvement of the flexibility and of the flushing flow. For further cross section reduction, it is provided in this context that the employed laser fiber comprises no buffering (protective coating) but only the core, comprised of material with higher refractive index, and the surrounding cladding or clad glass that is comprised of a dielectric material with lower refractive index. By eliminating the buffering, the stiffness is reduced and thus the flexibility of the instrument further improved. The tasks of buffering, such as e.g. bending protection, are taken over by the inner tube that surrounds the laser fiber.

The presently employed terms "distal" and "proximal" for describing positional information at the instrument are to be understood in relation to the user of the instrument, i.e., "distal" is an instrument part that is farther away from the user who operates the instrument at the handle while "proximal" in contrast thereto means an instrument part that is positioned closer to the user. Therefore, the end region of the instrument with the working tip of tool and light guide exit end are referred to as "distal" and the end region of the instrument with the handle and its end section where the optical waveguide is decoupled for connection to a light source as "proximal". Based thereon, "distal" refers to locations, sections or directions which are positioned at or closer to the working tip while "proximal" describes locations, sections or directions that are located at or closer to the decoupling handle end.

In a further embodiment, the handle of the medical instrument can comprise a handle body and at least an actuation element for actuating the tool that can be in particular a stone basket. For this purpose, a proximal end section of the outer tube is connected to the actuation element while a proximal end section of the inner tube which projects in the handle past the proximal end of the outer tube is stationarily supported in the handle so that the outer tube can be axially displaced relative to the inner tube for actuating the tool by means of the actuation element. Alternatively, it is however also conceivable that, in reverse, a proximal end section of the outer tube is supported in the handle and a proximal end section of the inner tube, which projects in the handle past the proximal end of the outer tube, is connected to the actuation element so that the inner tube is axially displaceable relative to the outer tube for actuation of the tool by means of the actuation element.

For example, the actuation element can be a handle slide in an embodiment which, for movement of the outer (or inner) tube in axial direction, can be displaced relative to the handle body. An actuation element as an alternative thereto can be, for example, an adjusting wheel.

As an alternative or in addition, in the embodiment in which the actuation element is connected to the proximal end section of the outer tube, this connection can be provided by a slide sleeve which is connected to the actuation element and in which a connection sleeve is supported in which the outer sleeve is fastened. By such a connection sleeve, the connection surface with the outer tube extends across a longer axial section, whereby the displacement of the outer tube relative to the inner tube is assisted. In principle, however, the actuation element can also be directly connected to the proximal end section of the outer tube or fastened thereat.

In a further embodiment, it can be provided that the support of the proximal end section of the inner tube in the handle is provided by a fixation sleeve in which the inner tube is fastened and which rests with its distal end against a support device that is provided between the proximal end of the outer tube and the fixation sleeve in the handle body or in a handle body attachment that adjoins a proximal end of the handle body. With the fixation sleeve that is resting against this support device, an entrainment of the inner sleeve upon displacement of the outer sleeve in distal direction is prevented so that the wire ends of the tool can be displaced relative to each other.

Such a support device can be simply an annular shoulder in the handle body or in a handle body attachment against which the fixation sleeve is resting. In a preferred embodiment, it is however provided that the support device provides at the same time an overload protection and is provided by a spring (coil spring) wherein the fixation sleeve is resting against its proximal end, wherein the distal end of the spring is supported at an annular shoulder provided in the handle body. Due to this sprung support, the fixation sleeve is held in its position by the inherent tension or pretension of the spring up to a predetermined force action upon displacement of the outer sleeve for actuation of the tool. When this predetermined force is surpassed, for example, when in case of a large stone which has been captured in a stone basket it is attempted to close the stone basket so that the pulling forces acting on the wire slings threaten to become too large, the fixation sleeve and thus the inner tube are moved against the spring in distal direction in order to prevent damage to the wire slings.

The annular shoulder at which the distal end of the spring is supported in the handle body can be provided in this context in a preferred embodiment by a proximal end of a guide sleeve that is arranged in the handle body and provides for guiding of the slide sleeve that is connected to the handle slide. In this way, the outer tube, which is supported by the connected connection sleeve in the slide sleeve, is guided safely in axial direction upon displacement.

Furthermore, in a further embodiment it is provided that the optical waveguide projects past the proximal end of the inner tube and extends through the proximal axial end section of the handle out of the handle for connection to a laser light source, preferably a thulium laser. The proximal axial end section in this context can comprise in a preferred embodiment an annular seal lip that is contacting seal-tightly around the optical waveguide. Particularly preferred, this annular seal lip can be radially adjustable or can comprise, as in case of an aperture, a radially adjustable opening cross section so that the sealing force that is acting on the circumference of the laser fiber can be adjusted. Such axial end sections with adjustable seal lip that are actuated by a rotatable housing section are obtainable as Tuohy-Borst adapter.

Preferably, this sealing force can be adjusted such that, according to a further embodiment, an axial displacement of the optical waveguide in the inner tube is possible without damaging the laser fiber. As an alternative, the seal can be somewhat released for displacement of the laser fiber, i.e., the cross section of the seal can be opened and closed again after completed positioning. In a preferred embodiment of the axially displaceable optical waveguide which is arranged in the inner tube, the handle can have a second actuation element in order to provide for displacement of the optical waveguide in a simple and comfortable way. This second actuation element can comprise, or can be connected to, a displacement device which is in operative connection with the optical waveguide and which provides for an axial displacement of the optical waveguide. Here also, handle slides or adjusting wheels are conceivable as suitable actuation elements. Preferably, the second actuation device for displacement of the optical waveguide can be provided in the region of the proximal axial end section of the handle body, for example, between the decoupling end and the sealing lip or between the sealing lip and the fixation sleeve.

In principle, the handle can furthermore comprise an insertion aid for the optical waveguide into the inner tube which, at its proximal end, comprises an e.g. funnel-shaped insertion opening which tapers toward the inner cross section of the inner tube and which simplifies insertion of the optical waveguide into the inner tube upon assembly of the medical instrument. Such an insertion aid can be provided in an expedient manner at the proximal handle end or at least at the proximal end of the fixation sleeve or at another device that fixes the inner tube.

The tool of a medical instrument according to the invention which is embodied as a wire structure can be a grasping tool of a single wire sling that is formed of a first and a second wire section connected thereto, wherein a proximal end of the wire sling is connected to the inner tube and the other proximal end of the wire sling is connected to the outer tube.

A preferred embodiment of the medical instrument provides as a wire structure tool a stone basket with which concrements such as kidney or gall stones can be captured that are to be broken up by laser beams from the coaxially arranged optical waveguide. In this context, a medical instrument according to the invention can be provided with different stone baskets. The stone basket can be formed of two or three wire slings that are each formed of a first wire section and a second wire section connected thereto. In this context, each wire sling can be fastened with a first proximal end to the inner tube and with a second proximal end to the outer tube. In this way, the stone basket in one embodiment can be a closed stone basket that is formed of two wire slings of which each wire sling is comprised as one piece of a first and a second wire section connected thereto. The wire slings can cross or contact each other in a region that is oppositely positioned to the exit end of the optical waveguide in order to close the stone basket in this way. The wire slings can preferably be connected to each other at this crossing or contact point.

As an alternative, a closed stone basket can be comprised of four separate wire sections, for example, two first and two second wire sections so that two first wire sections at their proximal end are connected to the inner tube, respectively, and two second wire sections are fastened at their proximal end to the outer tube, respectively, while the other distal ends of the wire sections are connected to each other, as needed by use of a cap-shaped tip or a connecting surface, in a region that corresponds to the crossing or contact point that is positioned opposite the exit end of the optical waveguide. In this context, the two first and the two second wire sections can each be adjacently positioned or preferably symmetrically oppositely arranged.

As needed, it is however also conceivable that a closed stone basket can be formed asymmetrically of one first and three second wire sections or three first and one second wire section, wherein the first or the three first wire sections at their proximal end are connected to the inner tube and the corresponding three second wire sections or one second wire section are/is connected at the proximal end to the outer tube.

In a further alternative embodiment, the four wire sections that from a closed stone basket can be realized as one piece by a single wire which is bent at three uniformly spaced-apart bending locations in alternating directions at an acute angle so that the single wire is divided into four continuous wire sections of which two respective neighboring wire sections form a wire sling, respectively. In this context, the first and third bending location can be positioned in the region that is positioned opposite the exit end of the optical waveguide and can be connected there, while the free wire ends of the single wire form both proximal ends either of a first or second wire section that are attached to one of the inner and outer tube and the second bending location essentially forms the corresponding proximal ends either of a second or first wire section that are fastened respectively to the other one of the inner and outer tube. It is conversely however also conceivable that the first and third bending location, arranged proximal, are fastened respectively to the inner and the outer tube while the free ends and the second bending location are connected distally in the region that is opposite to the exit end of the optical waveguide.

In a particularly preferred embodiment, the stone basket of a medical instrument according to the invention can be formed as an open stone basket that preferably comprises three wire slings, each with a first and a second wire section, that are circumferentially arranged adjacent to each other without crossing each other. In an embodiment that is preferred in this context, a first wire section, fastened with the proximal end to the inner tube, of each wire sling together with a second wire section, fastened with the proximal end to the outer tube, of the respective neighboring wire sling can be guided in a common envelope with which opening and closing of the stone basket is guided. Each envelope can be a sleeve with two passage openings for the respective wire section. In this context, the envelopes can also be fastened to the outer tube, for example, by means of a shrink hose section, or they can be present without being fastened. The loose envelopes provide the advantage that the stone basket can open farther because the bending locations of the wire slings at the connection to the tubes are exposed. Due to the attachment of the envelopes at the outer tube, on the other hand, sliding of the envelopes is safely prevented which otherwise could lead to hindrance when actuating the stone basket.

In principle, closed and open stone baskets or other grasping tools with a number of wire sections deviating from two or three are conceivable according to the invention and are to be encompassed in corresponding modifications of the aforementioned embodiments.

In a preferred embodiment, the wire sections that from the wire structure are of nitinol and can comprise a pretension for the open position of the tool or stone basket. For improving the stability and the functionality, the wire sling(s) can be embodied at least partially as flat wire.

In order to enable a sterilization of the medical instrument without risk of deformation, it is provided in a further embodiment that the outer tube is manufactured of a heat-resistant plastic material. An example for this are polyimides that, in addition to their chemical resistance, comprise a high heat resistance with continuous operation temperatures of up to 230° C. and temporarily up to 400° C.

In a preferred embodiment, the inner tube can comprise a fiber reinforcement for bending or buckling protection of the catheter as a whole and in particular of the optical waveguide, the fiber reinforcement provided, at least at the exterior side, with a friction-reducing plastic coating (e.g. polytetrafluoroethylene) in order to assist in a friction-reduced relative movement between the inner and the outer tube. The fiber reinforcement that is configured, for example, as a meshwork, can preferably comprise metal fibers or can be comprised thereof; however, reinforcement fibers of other materials such as plastic materials (e.g. aramid), carbon but also glass fibers are also conceivable because they are embedded in the tube, even though the latter are not preferred because they are very brittle.

Depending on the material of the outer tube, the attachment of the proximal ends of every second wire section at the outer tube can therefore be realized by gluing (e.g. epoxy, polyurethane or silicone adhesive), fusing or welding (by induction, vibration or ultrasound). Preferably, as an alternative or in addition thereto, a shrink hose section can be applied over a connection section at the end of the outer tube and the proximal ends of the at least one second wire section.

The attachment of the proximal ends of each first wire section to the inner tube can be realized in an equivalent manner also by gluing (e.g. epoxy, polyurethane or silicone adhesive), fusing or welding (by induction, vibration or ultrasound) and/or an additional shrink hose section that extends across a connection section at the end of the inner tube and the proximal ends of each first wire section.

Attachment forms of the proximal ends of each first wire section to the inner tube that are alternative thereto are also available by means of the fiber reinforcement of the inner tube. For example, the wire ends of the fiber reinforcement at the distal end of the inner tube or at least some of these fiber ends can be connected frictionally and/or material-fused to the proximal ends of each first wire section. A friction connection is understood herein as all types of knotting, intertwining, interlocking by means of which a satisfactory friction connection between the fiber ends and the proximal ends of each first wire section can be produced. The material-fused connection can be realized by gluing or welding wherein preferably the fibers of the fiber reinforcement can be metal fibers that, particularly preferred, can consist of a material corresponding to the wire sections.

When the fiber reinforcement of the inner tube comprises fibers of a material or is comprised thereof that corresponds to the metal of the wire sections, e.g. of nitinol, an integral connection of the proximal ends of each first wire section to the inner tube can be conceivable also in that the at least one first wire section is formed of at least some of the metal fiber ends of the fiber reinforcement of the inner tube.

A method according to the invention for producing a medical instrument according to the invention provides the following steps:
  forming a tool of at least two wire sections to a wire structure and providing a catheter assembly of an outer tube and an inner tube that is coaxially arranged thereto and movable relative thereto,
  fastening a proximal end of at least one first wire section to the distal end of the inner tube, and
  fastening a proximal end of at least one second wire section to the distal end of the outer tube so that the tool can be actuated for opening and closing by the relative movement between the outer tube and the inner tube without guide wire, and
  coaxial insertion of the optical waveguide in and through the inner tube so that an exit end of the optical waveguide ends coaxially in a space delimited by the tool. The insertion of the optical waveguide is carried out at the end in order to avoid damage thereto during the assembly of the instrument. Preferably, the insertion of the optical waveguide into the inner tube can be realized in an axially stretched position of the entire catheter assembly in order to avoid damage to the optical waveguide as well as to the tube assembly.

In a further embodiment of the method, prior to the insertion of the optical waveguide, the steps can be performed:
  providing the optical waveguide without buffering or removing the buffering from the optical waveguide, and/or
  providing a handle with a handle body and at least one actuation element for actuating the tool, and
  connecting a proximal end section of the outer tube to the actuation element, and supporting a proximal end section of the inner tube, which is projecting in the handle past the proximal end of the outer tube, in the handle so that the outer tube for actuation of the tool by means of the actuation element is axially displaceable relative to the inner tube.

BRIEF DESCRIPTION OF THE DRAWINGS

Further embodiments as well as some of the advantages which are associated with these and further embodiments be become clear and better understood by means of the following detailed description with reference to the accompanying Figures. Objects or parts thereof which are substantially identical or similar may be provided with the same reference characters. The Figures are only a schematic illustration of an embodiment of the invention.

It is shown in:

FIG. 8 perspective views a), b) of alternatively embodied tools with a wire sling of a medical instrument according to the invention;

FIG. 9 a perspective view of a situation of use of a medical instrument according to the invention with the working tip with stone basket and laser extending from a working channel of an endoscopic instrument.

DESCRIPTION OF PREFERRED EMBODIMENTS

The invention concerns a medical instrument that employs at the same time a tool and an optical waveguide. In this context, the tool can be, for example, a grasping tool such as a stone basket that is combined with a coaxially arranged optical waveguide, e.g., a laser fiber as a lithotripter.

The optical waveguide, as a result of the employed thulium laser technology and of the embodiment according to the invention without buffering and due to the actuation of the tool without guide wire, can be embodied with significantly reduced diameter in comparison to conventional coaxial lasers and comprises thus a significantly improved flexibility with simultaneous good permanent and bending stability. In this context, the inner tube of the catheter assembly takes on a multi-functionality and provides, in addition to the protection of the optical waveguide, the stability of the catheter assembly and forms at the same time a part of the actuation mechanism of the tool.

Figure 1:
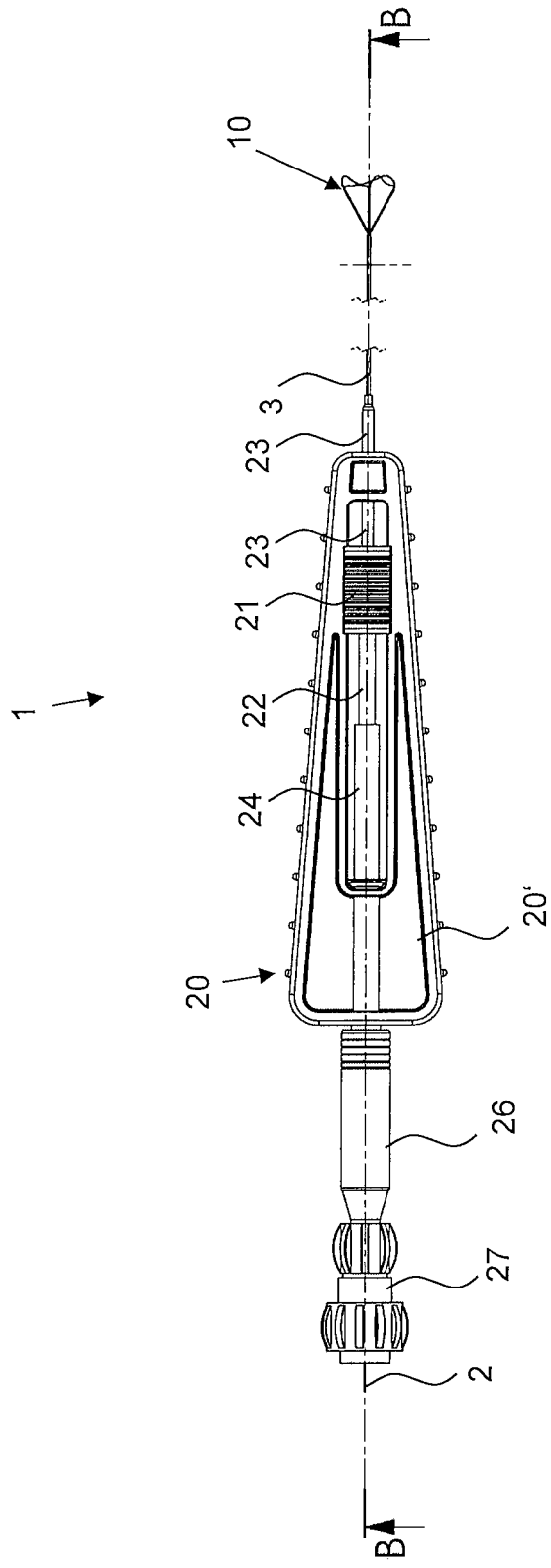
FIG. 1 a plan view of the medical instrument in an embodiment according to the invention.
Figure 2:
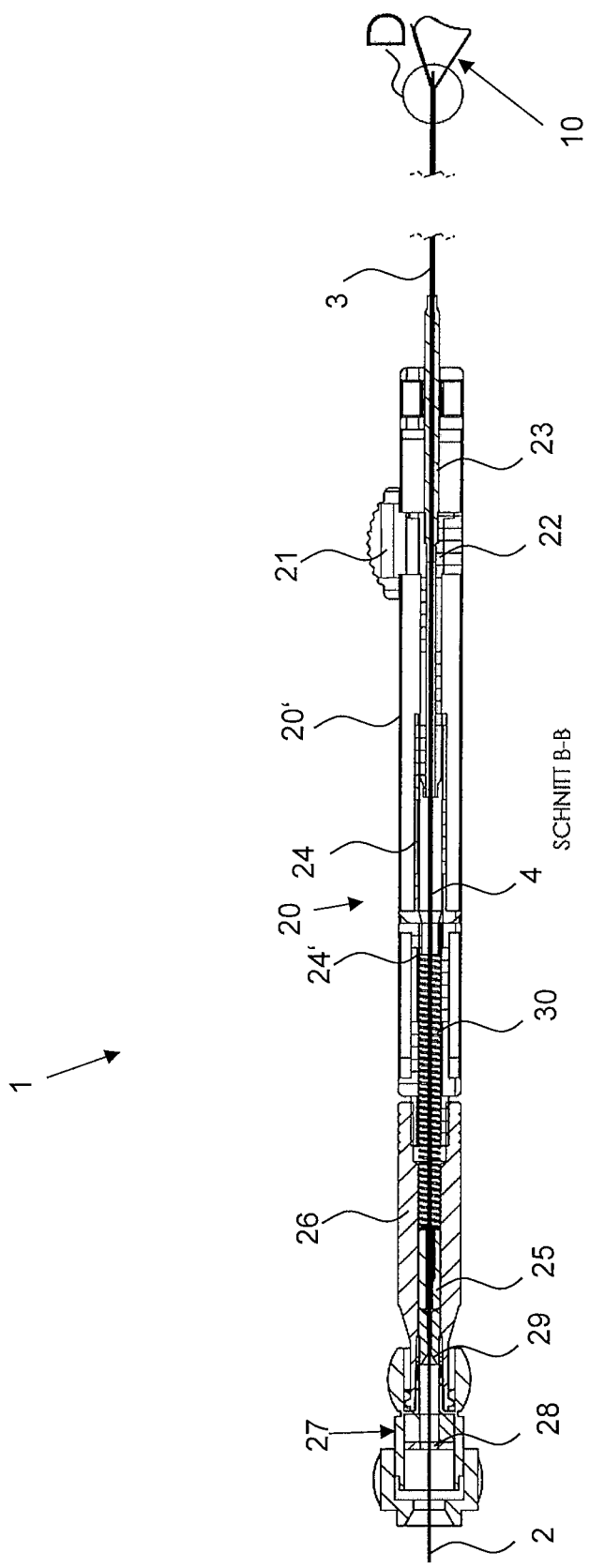
FIG. 2 a section view through the medical instrument of FIG. 1 along section line B-B.
Figure 3:
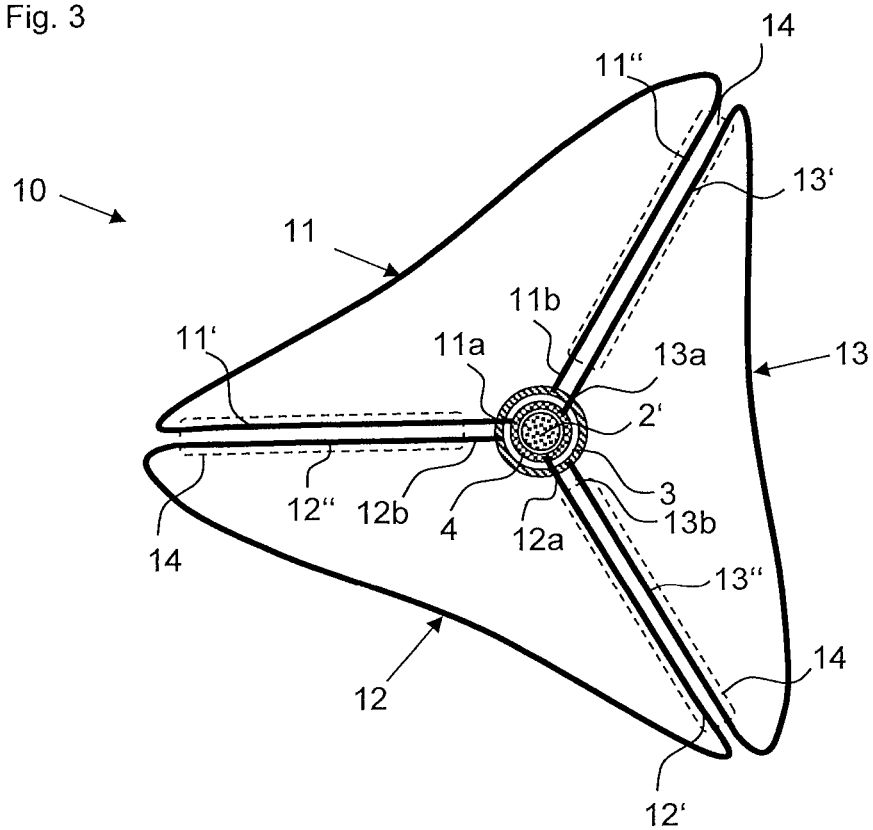
FIG. 3 an enlarged front view from the front of the stone basket of the medical instrument of FIG. 1.
Figure 4:
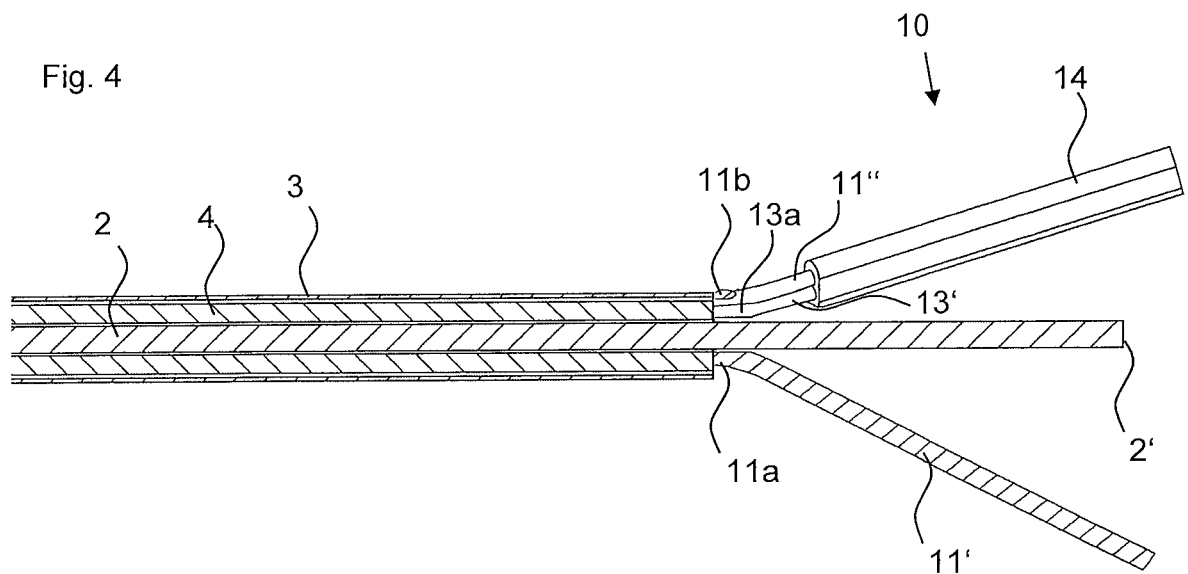
FIG. 4 a detail section view of the detail D of FIG. 2.

Important for the elimination of a guide wire for a medical instrument 1, as illustrated in FIGS. 1 and 2, is the attachment of the tool 10, that is formed of connected wire sections, with the proximal wire ends to the distal ends of the outer and inner tubes 3, 4 of the catheter assembly. FIGS. 3 and 4 show this in detail with the example of an open stone basket 10 of the instrument 1 of FIGS. 1, 2 with three wire slings 11, 12, 13. The three wire slings 11, 12, 13 form each in plan view approximately a triangle with a first wire section 11', 12', 13' whose proximal ends 11a, 12a, 13a are fastened to the inner tube 4 and with a second wire section 11", 12", 13", whose proximal end 11b, 12b, 13b is connected to the outer tube 3. A wire section of each wire sling 11, 12, 13 that connects the first wire sections 11', 12', 13' and second wire sections 11", 12", 13", respectively, is not provided with reference characters herein.

In FIG. 3, for reasons of simplification of the illustration, a significant distance between the outer tube 3 and the inner tube 4 is shown in order to more clearly illustrate the principle of the connections of the proximal ends 11a, 12a, 13a, 11b, 12b, 13b to the respective outer and inner tube 3, 4. Between the outer and inner tube 3, 4, as between the inner tube 3 and the optical waveguide 2, no significant radial clearance is provided. The diameters are selected so as to be matched such that the optical waveguide 2 can be inserted into the inner tube 4 and, as needed, can be displaced axially therein and that the outer tube 3 is axially moveable relative to the inner tube, but the coaxial arrangement of outer and inner tube 3, 4 with the optical waveguide 2 is ensured that determine the position of the tool 10 and enable that the optical waveguide ends coaxially in the tool 10.

So that the stone basket 10 can be actuated with the catheter tube assembly without guide wire, the proximal ends 11a, 12a, 13a of the first wire sections 11', 12', 13' of each wire sling 11, 12, 13 are fastened to the inner tube 4 in which the laser fiber 2 is coaxially guided so that the exit end 2' is positioned at the center of the stone basket 10 and an exiting laser beam extends coaxially, and the proximal ends 11b, 12b, 13b of the second wire sections 11", 12", 13" are fastened to the outer tube 3. So that the three-arm open stone basket 10 opens and closes in the desired manner, a first wire section 11', 12', 13' of each wire sling 11, 12, 13 is guided together with the second wire section 12", 13", 11" of the respective neighboring wire sling 12, 13, 11 in a common envelope 14. The envelope 14 that enables a longer service life and, with a suitable color and material selection, a better visibility is not fastened to the outer tube 3 in the illustrated example. Such an attachment, e.g. by means of a shrink sleeve section, can however be provided indeed in order to prevent sliding of the envelopes 14. Such a guide envelope 14 is not required for other tools or closed stone baskets 10 (compare FIGS. 6 to 9).

The arrangement illustrated here in detail of the proximal wire ends at the inner tube and at the outer tube can be applied to other embodiments of the tool with a deviating number of wire slings. Important in this context is that of the two ends of each wire sling one is fastened to the inner tube and one to the outer tube, respectively, in order to be able to deform the wire slings for actuation of the tool by a relative displacement of the tube assembly.

In general, the possibilities for attachment of the proximal ends of the wire sections at the outer and the inner tube can depend on the material of the tubes wherein the wire sections are preferably of metal, particularly preferred of nitinol, so that they can be embodied with a pretension for the open position of the tool.

The outer tube at which the proximal ends of the second wire sections are fastened is of a plastic material so that the proximal ends of the second wire sections can be fused into the distal tube end when the plastic material is a meltable thermoplastic material. However, since the outer tube can be preferably manufactured of a heat-resistant plastic material such as polyimides, some of which are not meltable, the proximal ends of the second wire sections can be fastened by means of adhesive and/or an additional shrink hose section (not illustrated) to the outer tube.

In principle, the proximal ends of the first wire sections can be fastened in the same manner, i.e., by means of adhesive and/or an additional shrink hose section, to the inner tube which—in contrast to the outer tube—can comprise a fiber reinforcement as a bending protection of the laser fiber guided therein. For reducing the friction at the outer tube for improved sliding upon relative movement between the outer and the inner tube, the fiber reinforcement can be provided at least on the outer side with a friction reducing plastic coating. For this purpose, a plastic material with a reduced friction coefficient such as, for example, polytetrafluoroethylene or the like, can be used. Advantageously, in this context, the static friction is of the same magnitude as the slide friction so that the relative movement between outer and inner tube can be performed without jerking.

Further possibilities are available for connection of the proximal ends of the first wire sections to the inner tube due to the fiber reinforcement. For example, open fiber ends at the distal end of the inner tube can be connected by friction to the proximal ends of the first wire sections, i.e., by knotting, intertwining, interlocking etc. The fiber ends can be connected by material fusion to the first ends, for example, by gluing. When the fibers of the fiber reinforcement are at least partially of metal, welding or soldering for connecting the fiber ends to the proximal ends of the first wire section are conceivable also. When the metal of the reinforcement fibers is the same metal as it is provided for the wire slings, an integral connection between the fiber reinforcement and the proximal ends of the first wire sections can be present in that the first wire sections are formed of the metal fiber ends of the fiber textile reinforcement of the inner tube or at least of some of these metal fiber ends.

FIGS. 1 and 2 illustrate the actuation of the stone basket 10 at the handle 20 which comprises for this purpose a handle slide 21 which is axially slidable relative to the handle body 20'. The handle 20 comprises moreover a handle body attachment 26 and an axial end section (Tuohy-Borst adapter) 27 that adjoin at the proximal end of the grip body 20' of the attachment 26, respectively, and serve for supporting the inner tube 4 in a fixation sleeve 25 and for sealing the laser fiber 2 with a sealing lip 28. The laser fiber 2 extends coaxially through the entire catheter assembly and the handle 20 and out of the proximal axial end section 27 in order to be able to be connected to a laser light source (thulium laser—not illustrated).

As can be seen in the section illustration in FIG. 2, the attachment of the outer tube 3 at the handle slide 21 is realized by means of a connection sleeve 23 which surrounds a proximal end section of the outer sleeve 3 and is fastened, e.g. glued, thereto. The connection sleeve 23 is supported in a slide sleeve 22 which is connected to the handle slide 21. In this example, the slide sleeve 22 is guided additionally in a guide sleeve 24 that is arranged proximal to the slide sleeve 22 in the handle body 20'. Through this guide sleeve 24, the inner tube 4 extends to the fixation sleeve 25 in which a proximal end section of the inner tube 4 is fastened. The fixation sleeve 25 is supported in a handle body attachment 26 which adjoins axially the proximal end of the handle body 20'. Handle body 20' and handle body attachment 26 can comprise corresponding thread sections for this. The fixation sleeve 25 is stationary in relation to the slidable outer tube 4, but supported with an overload protection. This is provided by a coil spring 30 that is contacted at its proximal end by the fixation sleeve 25 and whose distal end is supported at the annular shoulder 24' which is formed by the proximal end of the guide sleeve 24. The inherent tension or a pretension of the spring 30 determines the force up to which the fixation sleeve 25 remains stationarily supported. In order to avoid damage of the stone basket 10 by pulling forces that are too great, e.g., when a very large captured concrement prevents a further closing of the basket 10 upon forward sliding of the handle slide 21, the pulling forces which are acting in this context on the inner tube 4 cause a compression of the spring 30 by means of the fixation sleeve 25, i.e., the inner tube 4 follows the movement of the outer tube 3 for relief of the wire slings.

In this context, the stone basket 10 in the illustration is in the open position. By movement of the handle slide 21 in distal direction, i.e., forwardly in the direction of the stone basket 10, the stone basket 10 deforms into the closed position by sliding of the outer tube 3 relative to the inner tube 4 with the wire sling ends respectively connected thereto.

In other embodiments, actuation variants deviating therefrom are however conceivable also.

In the handle body attachment 26 proximal to the fixation sleeve 25 in which the proximal end of the inner tube 4 is fastened, an insertion aid 29 is arranged in order to facilitate insertion of the laser fiber 2 into the inner tube 4 upon assembly. The insertion aid 29 comprises for this purpose at its proximal end a funnel-type opening that tapers toward the inner diameter of the inner tube 4. For fixation and sealing of the laser fiber 2, an axial end section 27 such as a Tuohy-Borst adapter is arranged and fastened, for example, by means of corresponding thread sections, at the proximal end of the handle body attachment 26. Fixation and sealing of the laser fiber 2 is achieved by a radial seal lip 28 whose opening diameter can be adjusted by rotation of a housing section of the end section 27.

The handle illustrated in FIGS. 1 and 2 is only exemplary. Deviations in design and modifications of functional details are possible within the claimed subject matter. Thus, alternatives to the handle slide as actuation element for sliding the outer tube, such as e.g. an adjusting wheel that by transmission means transmits the rotational movement in axial translation, are conceivable as well as variants in which the inner tube can be moved relative to the outer tube so that the elements for actuation and for stationary but overload-protected support must be realized correspondingly in reverse.

Figure 5:
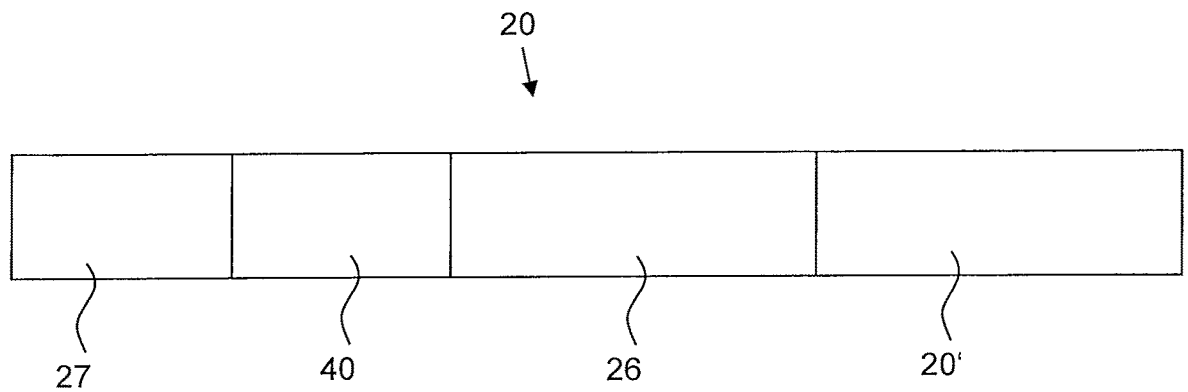
FIG. 5 a schematic illustration of an embodiment of the handle body of a medical instrument according to the invention.

FIG. 5 shows in a schematic manner an embodiment of a handle 20 that permits a displacement of the laser fiber 2 independent of the actuation of a tool 10, such as opening and closing of a stone basket, so that the laser fiber 2 can be separately manipulated. For this purpose, the handle 20 comprises a second actuation element 40 that in the illustrated example is provided between the handle body attachment 26, in which the insertion aid 29 and the fixation sleeve 25 are present, and the axial end section 27 with the seal lip 28. For this purpose, a further handle section can be inserted for integration of the actuation element 40 that comprises a slide device or is connected thereto in order to axially slide the laser fiber 2. For this purpose, structures such as handle slide or adjusting wheel with transmission means are conceivable similar to those that are provided for displacement of the outer tube 4.

FIGS. 6 to 9 show alternative tools 10 of a medical instrument 1 while in FIGS. 1 to 4 an open stone basket 10 with a three-arm embodiment as a tool 10 of the medical instrument 1 is illustrated. This open three-arm basket that represents a particularly preferred embodiment combines the advantages of a conventional basket such as safe capture of stones and fragments with those of a grasper that enables a simple new positioning of stones and represents thus an optimal tool for the removal of stones. This stone basket 10 as well as the other tools 10 of FIGS. 6 to 9 can be imparted with a high permanent stability by a flat wire design of the wire slings because the flat wire design effects a higher radial force that ensures improved functionality.

Figure 6:
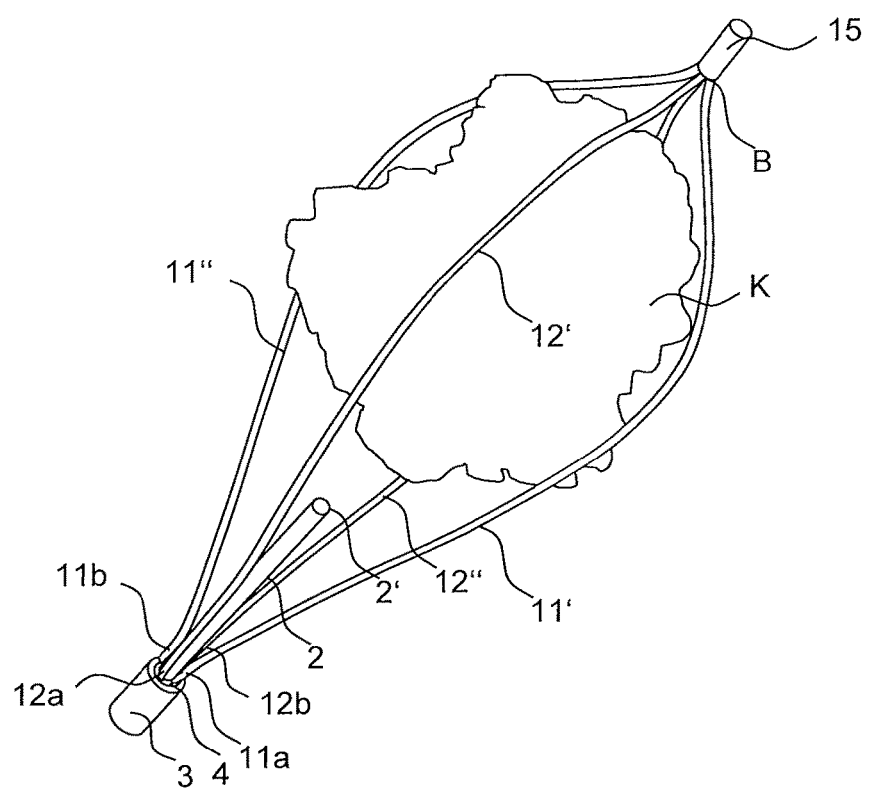
FIG. 6 a perspective view of an alternatively embodied stone basket of a medical instrument according to the invention.

In FIG. 6, a closed stone basket 10 with a captured stone (concrement) K is illustrated as tool 10. Since the optical waveguide 2 and the catheter assembly of inner tube 4 and outer tube 3 are coaxially arranged, the optical waveguide 2 ends exactly centrally or coaxially in the grasp tool 10 which significantly reduces the probability of hitting a tool structure when the object K that is grasped by the tool 10 is irradiated by a laser beam that is exiting from the optical waveguide 2. The stone basket 10 in FIG. 6 has a straight shape that imparts to the stone basket 10 an erection force as large as possible, with a cap-type tip 15 in which the wire sections 11', 11", 12', 12" are joined for forming the wire structure from essentially two symmetric wire slings in a region B opposite to the exit end 2' of the optical waveguide 2. In this context, the first wire elements 11', 12' at the proximal ends 11a, 12a are connected to the inner tube 4 and the second wire elements 11", 12" are connected at the ends 11b, 12b to the outer tube 3.

Figure 7:
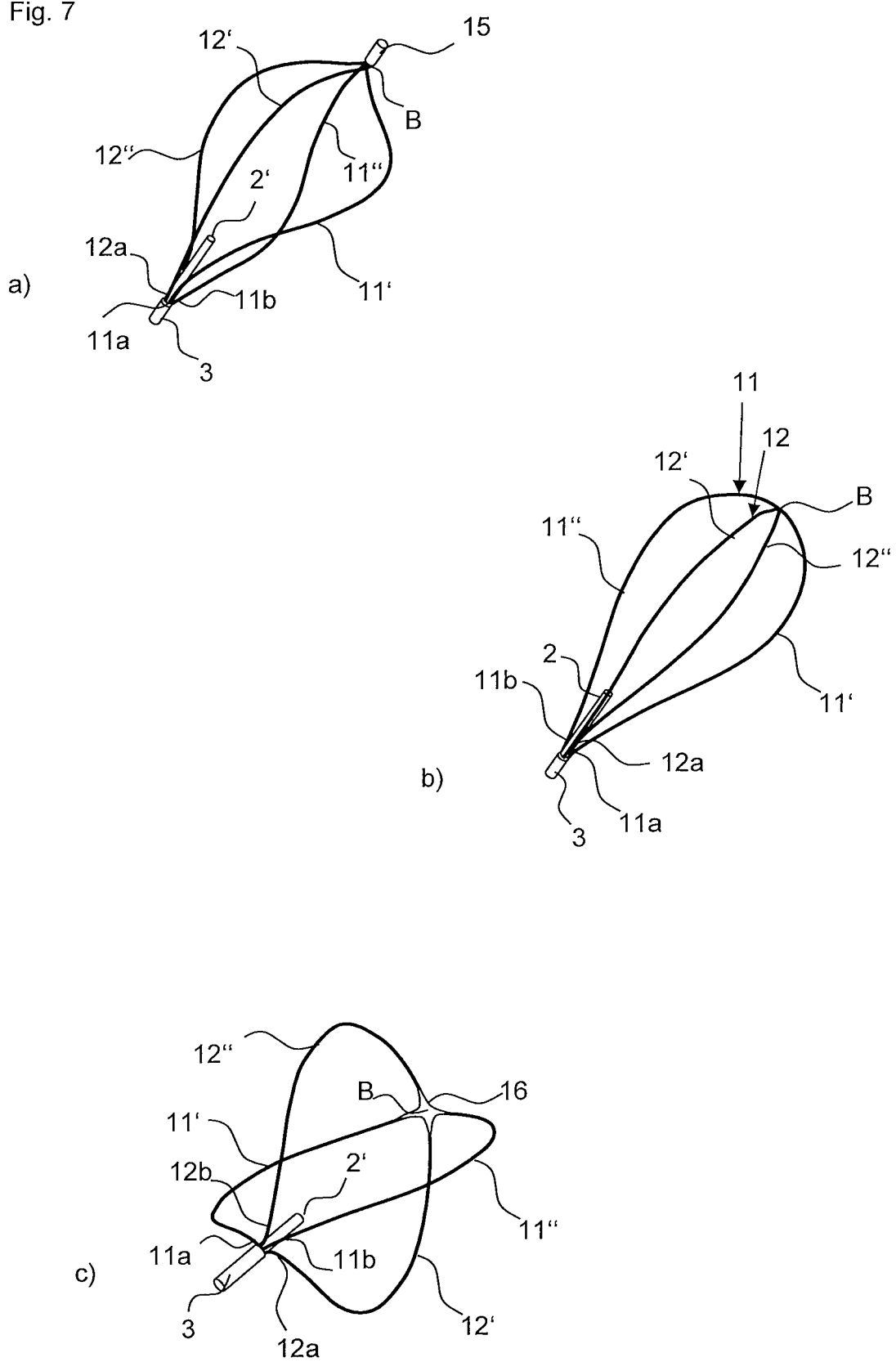
FIG. 7 perspective views a), b), c) of alternatively embodied stone baskets of a medical instrument according to the invention.

FIG. 7 shows three further embodiments a), b), c) of a closed stone basket 10 wherein here the details of the attachment of the wire sling ends at the outer tube 3 and the inner tube (not illustrated) are not illustrated for the purpose of simplifying the drawing. The stone basket 10 in FIG. 7a) corresponds to the basket of FIG. 6 with the exception that it comprises a helical shape, i.e., that the wire sections 11', 11", 12', 12" do not extend straight to the tip 15 but have a winding course. The helical shape enables an easier capture of a stone.

As an alternative to an embodiment of four separate wire sections 11', 11", 12', 12", the wire slings of a stone basket 10 with tip 15 can be manufactured of a single wire. In this context, the slings are formed by three uniformly spaced-apart acutely angled bending locations in alternating directions of the single wire that thus divide it into four continuous wires sections 11', 11", 12', 12" of which two neighboring wire sections 11', 11", 12', 12", respectively, form one of the wire slings, respectively. In the arrangement of such a closed stone basket 10 of a single wire at the distal end of the catheter assembly, there are two possibilities. Either the first and third bending location are arranged in the region B that is positioned opposite the exit end 2' of the optical waveguide 2 and connected to each other in the tip 15 so that the free wire ends of the single wire form proximal ends 11a, 12a of first wire sections 11', 12' or proximal ends 11b, 12b of second wire sections 11", 12" that are fastened at one of outer tube 3 and inner tube, wherein the second bending location forms the respective other proximal ends 11b, 12b of second wire sections 11', 12' or the proximal ends 11a, 12a of first wire sections 11', 12' that are fastened at the other one of outer tube 3 and inner tube. Or, alternatively, the first bending location can form the proximal ends 11a, 12a of the first wire sections 11', 12' and the third bending location the proximal ends 11b, 12b of the second wire sections 11", 12" (or, in reverse, the first bending location forms the proximal ends 11b, 12b of the second wire sections 11", 12" and the second bending location the proximal ends 11a, 12a of the first wire sections 11', 12') and be fastened respectively to the inner tube and the outer tube 3, while the free ends of the single wire and the second bending location in the region B that is positioned opposite the exit end 2' of the optical waveguide 2 are connected in the tip 15.

FIGS. 7b) and 7c) show respectively a stone basket 10 without a tip that enables a guiding action gentle to tissue with the rounded connection region B. In the illustrated examples, the stone basket 10 is comprised of two wire slings 11, 12 with wire sections 11', 11" and 12', 12" that are connected in one piece, respectively, wherein the proximal ends 11a, 12a of the first wire sections 11', 12' are connected to the inner tube (not illustrated) and the proximal ends 11b, 12b of the second wire sections 11", 12" to the outer tube 3. The stone basket 10 in FIG. 7c) comprises in this context in connection region B a connection location or surface 16 in the form of a diamond with concavely rounded sides. This connection location 16 can provide an improved endoscopic visibility when suitably colored.

In deviation from the illustrated examples, baskets with tip can also be formed of two wire slings or more, and baskets without tip can be formed of four or more separate wire sections or a single wire. In further deviation from the illustrated examples, closed stone baskets can also comprise an asymmetric number of first and second wire sections whose proximal ends then correspondingly are arranged asymmetrically at the outer and inner tubes. In this manner, a stone basket comprised of four wire sections can be fastened with a first wire section to the inner tube and with the three other second wire sections to the outer tube, or in reverse. Furthermore, closed stone baskets can also be formed of an uneven number of wire sections. In the stone basket of three wire sections, e.g. a first wire section can be connected at the proximal end to the inner tube and the two other second wire sections to the outer tube, or, in reverse, two first wire sections to the inner tube and a second wire section to the outer tube. With increasing number of wire sections, the number of possible arrangement variants increases correspondingly and are therefore not explained here in detail but are easily apparent to a person of skill in the art.

FIG. 8 shows two examples a) and b) with alternative tools 10 as working tip of a medical instrument according to the invention. In this context, the tool 10 is comprised of a wire sling 11 whose first wire section 11' is fastened at the proximal end 11a to the inner tube 4 and whose second wire section 11" at the proximal end 11b to the outer tube 3 of the catheter assembly. Here also, the laser fiber 2 ends centrally in the space which is delimited by the wire sling 11 which in FIG. 8a) is substantially embodied as an areal oval. Not illustrated are polygonal sling forms such as e.g. hexagon slings. FIG. 8b) shows a sickle-shaped sling 11 which delimits a shell-shaped space in which the laser fiber 2 ends coaxially. The wire sling 11 can be formed of a one-piece wire with two continuous wire sections 11', 11" or of two wire sections 11'; 11" connected to each other.

In FIG. 9, a situation of use of a medical instrument according to the invention with stone basket 10 is illustrated which has been opened through a working channel 101 of an insertion tube 100 of a ureteroscope, for example, at a location of use. In the illustrated example, the insertion tube 100 in addition comprises an illumination device 103 and a camera sensor 102 by means of which the user can observe the location of use. Due to the smaller dimension of the catheter assembly as a result of the employed thulium laser technology with the coaxially arranged optical waveguide 2 which can be embodied with an outer diameter (without buffering) of 150 μm to 200 μm (i.e., 130 μm to 180 μm core diameter and 10 μm cladding), the user has available more manipulation clearance in the working channel 101 and a maximum flushing flow for flushing can be obtained. In addition, the thulium laser technology enables an efficient lithotripsy at higher pulse rates. In relation to the laser power that is required for breaking up, theoretically laser fibers with even smaller diameters could be used, but then the stability and durability of the instrument suffers. And since already with laser fiber cross sections of 150 μm to 200 μm a very good flexibility of the instrument and a satisfactory flushing flow can be achieved, a further miniaturization of the fiber cross section of the optical waveguide for a minimal further increase of the flexibility represents no significant overall improvement because this would entail a significantly limited stability and durability.

In principle, the combined use of a stone basket with a laser lithotripter minimizes the stone retropulsion because the stone captured in the stone basket cannot yield upon impact of the laser pulse. Advantageously however, due to the coaxial arrangement that is now made possible by a miniaturized instrument, laser-induced damages at the wire slings are reduced because the laser pulse always impacts centrally on a captured concrement.

For producing a medical instrument according to the invention, first the catheter assembly of outer tube and inner tube, coaxially arranged thereto and relatively movable thereto, as well as the tool of a wire structure that is formed of at least two wire sections are provided. At least one proximal end of the wire sections of the wire structure is fastened to the distal end of the inner tube and at least one proximal end of the wire section of the wire structure to the distal end of the outer tube so that a relative movement between outer and inner tube effects opening and closing of the tool.

The proximal ends of the outer and inner tube are fastened with an actuation element in a suitable manner in a handle in order to be able to trigger the relative movement between the outer and the inner tube for opening and closing the tool. For this purpose, it is expedient that in the handle a proximal end section of the inner tube projects past a proximal end of the outer tube. In this context, for example, the proximal end section of the outer tube can be connected to the actuation element and the proximal end section of the inner tube can be supported stationarily in the handle so that the outer tube for actuation of the tool by means of the actuation element can be axially displaced in relation to the inner tube. The stationary support of the proximal end section of the inner tube can be embodied, as needed, for overload protection as a sprung support.

Only at the end, the optical waveguide, that is preferably used without buffering, so that first the buffering must be removed as needed, is coaxially inserted in and through the inner tube from its proximal end until the exit end of the optical waveguide at least closes off the distal end of the inner tube and thus can end coaxially in the space which is delimited by the tool. Since the proximal end of the inner tube is supported in the handle, it comprises at the proximal end a sealable opening for insertion of the optical waveguide. In addition, an insertion aid with a tapering insertion opening can be provided here in order to facilitate the threading action into the inner tube. In this context, for insertion of the optical waveguide for avoiding damages of the optical waveguide itself as well as of the inner and optionally outer tube, it is advantageous to position axially stretched the handle and the catheter assembly in order to facilitate the passing through action of the optical waveguide.

LIST OF REFERENCE CHARACTERS 1 medical instrument
2, 2' optical waveguide, exit end
3 outer tube
4 inner tube
10 tool, stone basket
11, 12, 13 wire sling
11a, 12a, 13a proximal end of the first wire section
11b, 12b, 13b proximal end of the second wire section
11', 12', 13' first wire sections
11", 12", 13" second wire sections
14 envelope
15 tip
16 connection location
20, 20' handle, handle body
21 actuation element/handle slide
22 slide sleeve
23 connection sleeve
24 guide sleeve
24' annular shoulder
25 fixation sleeve
26 handle body attachment
27 proximal axial end section/Tuohy-Borst adapter
28 seal lip
29 insertion aid for laser fiber
30 support device/spring
40 second actuation element
100 insertion tube
101 working channel
102 camera sensor
103 illumination
B region opposite the exit end
K concrement

What is claimed is:

1. A medical instrument with a tool, a catheter assembly, and a handle, with which the tool can be actuated,
    wherein the tool is a wire structure with at least two wire sections and is arranged at a distal end of the catheter assembly, which is comprised of an outer tube and an inner tube arranged coaxially thereto, wherein the outer tube and the inner tube are movable relative to each other,
    wherein the medical instrument moreover comprises an optical waveguide that extends through the inner tube and whose exit end ends coaxially in a space delimited by the tool,
    wherein the medical instrument comprises no guide wire for actuation of the tool,
    wherein at least a first wire section with a proximal end is fastened to a distal end of the inner tube and at least a second wire section with a proximal end is fastened to a distal end of the outer tube, and
    wherein the tool for opening and closing is actuatable by the relative movement between the outer tube and the inner tube.

2. The medical instrument according to claim 1, wherein the optical waveguide is a laser fiber that is configured for guiding laser radiation of a thulium laser, wherein the laser fiber comprises no buffering.

3. The medical instrument according to claim 1, wherein the handle comprises a handle body and at least one actuation element for actuation of the tool, and wherein:
- a proximal end section of the outer tube is connected to the at least one actuation element, and a proximal end section of the inner tube that projects in the handle past a proximal end of the outer tube is supported in the handle so that the outer tube is axially slidable relative to the inner tube by means of the actuation element for actuation of the tool, or
- a proximal end section of the outer tube is supported in the handle and a proximal end section of the inner tube that projects in the handle past a proximal end of the outer tube is connected to the actuation element so that the inner tube is axially slidable relative to the outer tube by means of the actuation element for actuation of the tool.

4. The medical instrument according to claim 3, wherein the actuation element is a handle slide that is slidable in an axial direction relative to the handle body for movement of the outer tube, and/or
wherein the connection of the actuation element to the proximal end section of the outer tube is provided by a slide sleeve that is connected to the actuation element and in which a connection sleeve is supported in which the outer tube is fastened.

5. The medical instrument according to claim 3, wherein the support of the proximal end section of the inner tube in the handle is provided by a fixation sleeve in which the inner tube is fastened and which is resting with its distal end against a support device that is provided between the proximal end of the outer sleeve and the fixation sleeve in the handle body or in a handle body attachment that adjoins a proximal end of the handle body.

6. The medical instrument according to claim 5, wherein the support device is a spring at whose proximal end the fixation sleeve is resting, and
wherein a distal end of the spring is supported at an annular shoulder that is provided in the handle body.

7. The medical instrument according to claim 6, wherein the annular shoulder is provided by a proximal end of a guide sleeve that is arranged in the handle body for guiding the slide sleeve.

8. The medical instrument according to claim 3, wherein the optical waveguide projects past a proximal end of the inner tube and extends through a proximal axial end section of the handle out of the handle, and
wherein the proximal axial end section comprises an annular seal lip that is contacting seal-tightly around the optical waveguide.

9. The medical instrument according to claim 8, wherein the annular seal lip is radially adjustable or comprises a radially adjustable opening cross section.

10. The medical instrument according to claim 1, wherein the optical waveguide is axially slidably arranged in the inner tube,
wherein the handle comprises a second actuation element that comprises a slide device or is connected thereto, that is operatively connected to the optical waveguide and provides for an axial displacement of the optical waveguide,
and/or
wherein the handle comprises an insertion aid with an insertion opening, tapering toward an inner cross section of the inner tube, for the optical waveguide in the inner tube.

11. The medical instrument according to claim 1, wherein the wire structure of the tool:
- is a wire sling, which is formed of a first wire section and a second wire section, or
- is a stone basket of two or three wire slings, which are each formed of a first wire section and a second wire section.

12. The medical instrument according to claim 1, wherein the wire structure is made of nitinol and comprises a pretension for the open position of the tool, and/or is provided at least partially by flat wire.

13. The medical instrument according to claim 1, wherein:
the outer tube is manufactured of a heat-resistant plastic material and/or
the inner tube comprises a fiber reinforcement with a friction-reducing plastic coating.

14. The medical instrument according to claim 13, wherein:
the fastening attachment of the proximal end of the at least one second wire section at the outer tube is provided by gluing, fusing and/or an additional shrink hose section that extends across a connection section at the distal end of the outer tube and the proximal end of the at least one second wire section,
and/or
the fastening attachment of the proximal end of the at least one first wire section at the distal end of the inner tube:
a) is provided by gluing, fusing and/or an additional shrink hose section that extends across a connection section at the distal end of the inner tube and the proximal end of the at least one first wire section, or
b) is provided by a friction and/or material-fused connection of the proximal end of the at least one first wire section with fiber ends of the fiber reinforcement which are present at the distal end of the inner tube.

15. The medical instrument according to claim 13, wherein the fiber reinforcement is a metal fiber reinforcement.

16. The medical instrument according to claim 15, wherein:
the fastening attachment of the proximal end of the at least one second wire section at the outer tube is provided by gluing, fusing and/or an additional shrink hose section that extends across a connection section at the distal end of the outer tube and the proximal end of the at least one second wire section,
and/or
the fastening attachment of the proximal end of the at least one first wire section at the distal end of the inner tube:
a) is provided by gluing, fusing and/or an additional shrink hose section that extends across a connection section at the distal end of the inner tube and the proximal end of the at least one first wire section, or
b) is provided by a friction and/or material-fused connection of the proximal end of the at least one first wire section with fiber ends of the fiber reinforcement which are present at the distal end of the inner tube, or
c) is provided by an integral connection of the at least one first wire section with the metal fibers of the fiber textile reinforcement of the inner tube, wherein the at least one first wire section is formed of at least some of the metal fiber ends of the fiber textile reinforcement of the inner tube.

17. A method for producing a medical instrument according to claim 1, comprising the steps of:

forming the tool of the at least two wire sections to the wire structure and providing the catheter assembly of the outer tube and the inner tube coaxially arranged thereto and movable relative thereto, fastening the proximal end of the at least one first wire section to the distal end of the inner tube, fastening the proximal end of the at least one second wire section to the distal end of the outer tube so that the tool is actuatable for opening and closing by the relative movement between the outer tube and the inner tube without guide wire, and coaxially inserting the optical waveguide into and through the inner tube so that the exit end of the optical waveguide ends coaxially in the space delimited by the tool.

18. The method according to claim 17, comprising the steps, prior to insertion of the optical waveguide, of:

providing the optical waveguide without buffering or removing a buffering from the optical waveguide, and/or providing the handle with a handle body and at least one actuation element for actuating the tool, connecting a proximal end section of the outer tube to the at least one actuation element, and supporting in the handle a proximal end section of the inner tube that projects in the handle past a proximal end of the outer tube so that the outer tube is axially slidable by means of the actuation element relative to the inner tube for actuation of the tool.

\* \* \* \* \*